(12) United States Patent
Godavarthy et al.

(10) Patent No.: US 8,664,448 B2
(45) Date of Patent: Mar. 4, 2014

(54) PROCESS FOR THE PRODUCTION AND PURIFICATION OF PROPYLENE GLYCOL

(75) Inventors: Srinivasa Godavarthy, Spring, TX (US); Wei-Yang Su, Spring, TX (US); Ralph M. DiGuilio, Spring, TX (US); Stan Harville, The Woodlands, TX (US); Matthew W. Forkner, Spring, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 533 days.

(21) Appl. No.: 12/994,961

(22) PCT Filed: Jun. 2, 2009

(86) PCT No.: PCT/US2009/045912
§ 371 (c)(1), (2), (4) Date: Nov. 29, 2010

(87) PCT Pub. No.: WO2009/149047
PCT Pub. Date: Dec. 10, 2009

(65) Prior Publication Data
US 2011/0112335 A1    May 12, 2011

Related U.S. Application Data

(60) Provisional application No. 61/059,070, filed on Jun. 5, 2008.

(51) Int. Cl.
*C07C 29/80* (2006.01)
*C07C 31/20* (2006.01)

(52) U.S. Cl.
USPC .......................................... 568/361; 568/862

(58) Field of Classification Search
USPC ................................... 568/861, 862
See application file for complete search history.

(56) References Cited

U.S. PATENT DOCUMENTS

| 5,214,219 | A | 5/1993 | Casale et al. |
| 5,426,249 | A | 6/1995 | Haas et al. |
| 5,616,817 | A | 4/1997 | Schuster et al. |
| 6,461,423 | B1 * | 10/2002 | Beall et al. ............... 106/487 |
| 2007/0287865 | A1 | 12/2007 | Arredondo et al. |
| 2008/0315151 | A1 | 12/2008 | Suppes et al. |

FOREIGN PATENT DOCUMENTS

WO    WO 2005/095536    10/2005

* cited by examiner

*Primary Examiner* — Sikarl Witherspoon
(74) *Attorney, Agent, or Firm* — Huntsman International LLC

(57) ABSTRACT

The present invention relates to a process for producing an odorless and colorless industrial grade propylene glycol from glycerol obtained during the manufacturing of biodiesel. The process includes hydrogenating the glycerol to form a hydrogenated product, distilling the hydrogenated product to form a glycol product, and contacting the glycol product with a treatment bed. The propylene glycol may be used in various industrial and consumer applications and products such as personal care products.

3 Claims, 1 Drawing Sheet

PROCESS FOR THE PRODUCTION AND PURIFICATION OF PROPYLENE GLYCOL

CROSS-REFERENCE TO RELATED APPLICATION

This application is the National Phase of International Application PCT/US2009/045912 filed Jun. 2, 2009 which designated the U.S. and which claims priority to U.S. Provisional Pat. App. Ser. No. 61/059,070 filed Jun. 5, 2008. The noted applications are incorporated herein by reference.

STATEMENT REGARDING FEDERALLY SPONSORED RESEARCH OR DEVELOPMENT

Not applicable.

FIELD OF THE INVENTION

The present invention described herein generally relates to a process for producing propylene glycol from glycerol derived from manufacturing biodiesel.

BACKGROUND OF THE INVENTION

The production of biodiesel occurs through the reaction of vegetable oils or animal fats with an alcohol in the presence of a catalyst to yield methyl esters (biodiesel) and glycerol. It's estimated that for every 9 kg of biodiesel produced, about 1 kg of by-product glycerol is formed. Thus, as biodiesel production increases, it's expected that large quantities of glycerol will become more readily available. It has therefore become desirable to develop effective refinement processes to convert such glycerol to value added commodity and specialty products, such as diols and other polyols, ketones, aldehydes, carboxylic acids and alcohols.

In particular, one such product is propylene glycol which is a widely used chemical in many industrial and consumer products. Traditionally produced by the hydration of petroleum-derived propylene oxide, various processes have recently been proposed for producing propylene glycol from glycerol. For example, U.S. Pat. No. 5,426,249 describes a process for simultaneously producing 1,2- and 1,3-propanediol by dehydrating gaseous glycerol to acrolein, hydrating the acrolein to 3-hydroxypropionaldehyde and subsequently hydrogenating the 3-hydroxypropionaldehyde in the presence of a conventional hydrogenation catalyst. U.S. Pat. Nos. 5,214,219 and 5,616,817 describe processes in which glycerol is hydrogenated to 1,2-propanediol using a copper/zinc or copper/cobalt catalyst at elevated temperatures and pressure. Finally, WO 05/095536 describes a process for converting glycerol to propylene glycol via an acetol intermediate at temperatures between about 150°-250° C. and a pressure of about 1-25 bar.

One drawback to the current processes is the formation of impurities and by-products during conversion that can cause undesirable color as well as odor in the propylene glycol product.

Thus, it is an object of the present invention to provide a process of reducing color and/or odor from the converted propylene glycol by essentially removing impurities and by-products produced during the conversion process. In addition, it is also an object of the present invention to provide an improved process for producing propylene glycol from glycerol at high selectivity and conversion and reduced operating costs.

SUMMARY OF THE INVENTION

The present invention relates to a process for producing an odorless and colorless industrial grade propylene glycol by hydrogenating a glycerol stream in the presence of a hydrogen-containing cycle gas and a hydrogenation catalyst to form a hydrogenated product, distilling the hydrogenated product to form a glycol product and contacting the glycol product with a treatment bed.

In another embodiment, the present invention relates to a process for producing an odorless and colorless industrial grade propylene glycol product by providing a hydrogenation reactor effluent comprising propylene glycol and glycerol to a hydrogenation reactor and hydrogenating the hydrogenation reactor effluent in the presence of a hydrogenation catalyst and hydrogen-containing cycle gas to form a hydrogenated product, distilling the hydrogenated product to form a glycol product, and the glycol product contacting the glycol product with a treatment bed to produce the industrial grade propylene glycol product.

The industrial grade propylene glycol produced according to the present invention may be used in various industrial and consumer applications and products, including personal care products.

BRIEF DESCRIPTION OF DRAWINGS

The use of the same reference symbols in different drawings indicates similar or identical items.

DETAILED DESCRIPTION OF THE INVENTION

Various embodiments of the present disclosure generally relate to a process for producing propylene glycol from glycerol. In particular, certain embodiments disclosed herein relate to a process for hydrogenating glycerol in a hydrogenation reactor to obtain a hydrogenated product, distilling the hydrogenated product to remove low boiling impurities and obtain a glycol product, and contacting the glycol product with a treatment bed to produce industrial grade propylene glycol that is odorless and colorless. Thus, the industrial grade propylene glycol produced according to the process of the present invention is substantially free of odor molecules perceived by the unaided nose and substantially free of colorants visible to unaided eye. By "substantially free" is meant that odors and colors are not present such that the unaided nose and eye cannot detect odors or colors. This means generally that from 0 to less than 0.001% of odor causing compounds and from 0 to less than 0.01% colorants are present. Odor causing compounds may include, but are not limited to, hydrocarbons, alcohols, ketones, aldehydes, acetates, organic acids and esters. Colorants may include, but are not limited to, unsaturated compounds, acetals and other carbonyl compounds, and peroxides. By "industrial grade" is meant the propylene glycol contains less than 2000 ppm of ethylene glycol.

Figure 1:
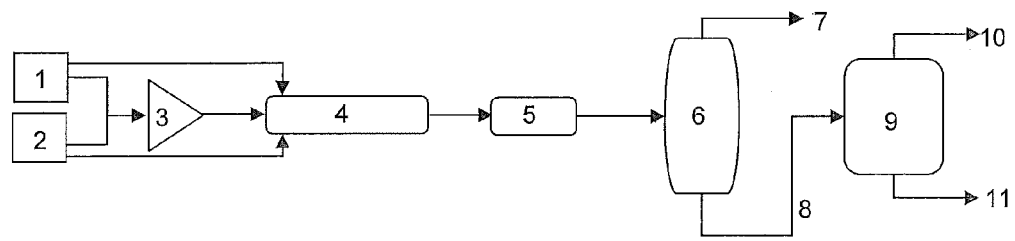
FIG. 1 and FIG. 2 and FIG. 3 include flow diagrams illustrating exemplary processes.

In one embodiment, the process of the present invention includes hydrogenating glycerol in the presence of a cycle gas and a hydrogenation catalyst in a hydrogenation zone to form a hydrogenated product. Referring to FIG. 1, a glycerol stream (1), derived from a biodiesel manufacturing process, may be provided stepwise or continuously to a first hydrogenation reactor (4) within the hydrogenation zone. As used herein, "biodiesel" refers to a mixture of fatty acid monoalkyl esters obtained from biogenic oil and/or fat-containing starting mixtures. The glycerol stream may contain impurities such as salts, organic materials, alcohols, acids and base. The amount of impurities may vary according to the method of production of the biodiesel. Therefore, the glycerol stream may be optionally pretreated prior to use. As used herein "pretreating" the glycerol stream may be carried out by a variety of methods, for example, filtration, absorbtion, membrane separation, electro-deionization or combinations thereof. In yet another embodiment, the glycerol stream may be preheated in a heat exchanger to a temperature within a range of about 20° C. to 300° C. prior to use.

According to certain embodiments, the glycerol stream may have a water content of not more than about 20% by weight, preferably not more than about 15% by weight, and more preferably not more than 5% by weight based on the total weight of the glycerol stream. In another embodiment, the glycerol stream is substantially anhydrous. By "substantially anhydrous" is meant a water content of not more than 1% by weight. The use of glycerol streams having a water content of not more than 20% by weight permits the preparation of propylene glycol in high yields and with high selectivity in the temperature and pressure ranges used during hydrogenation. In another embodiment, the glycerol stream contains from about 5-20% by weight water to reduce viscosity during hydrogenation.

According to another embodiment, the glycerol stream may have at least one organic solvent instead of or in addition to water. The glycerol stream may contain an organic solvent in an amount of not more than 20% by weight, preferably not more than 10% by weight, and more preferably not more than 5% by weight based on the total weight of the glycerol stream. Examples of organic solvents include methanol, ethanol, n-propanol, isopropanol, n-butanol, t-butanol, polyols and mono- and dialkyl ethers thereof, and cyclic ethers. Preferably, the glycerol stream does not contain organic solvent.

A cycle gas comprising hydrogen (2) may also be provided to the hydrogenation zone. In one embodiment, the hydrogen-containing cycle gas may be supplied directly to the first hydrogenation reactor. In another embodiment, the cycle gas and glycerol stream may be premixed in a mixer (3) and preheated in a heat exchanger to a temperature within a range of about 180°-230° C. prior to entering the first hydrogenation reactor. In addition to hydrogen, the cycle gas may also contain a minor amount of one or more inert gases, such as nitrogen, methane and other low molecular weight hydrocarbons, neon, and argon. The cycle gas may also contain condensable materials, such as water and methanol. Preferably, the cycle gas contains greater than 99%, and more preferably greater than 99.5% hydrogen.

Hydrogenation of the glycerol stream in the hydrogenation zone occurs in the presence of a hydrogenation catalyst. The hydrogenation catalyst is preferably a metal-containing catalyst and may comprise platinum, palladium, ruthenium, rhodium, iridium, copper, chromium, nickel, zinc, cobalt, cesium, manganese, silicon, aluminum, oxides thereof or combinations of any thereof. The hydrogenation catalyst may be a sponge or skeletal catalyst such as those referred to as a Raney catalyst. These include Raney copper and copper-containing metal alloys. In another embodiment, the hydrogenation catalyst may be reduced prior to use. Preferably the hydrogenation catalyst is a copper based catalyst such as copper/alumina/manganese, copper/chromite, copper/chromate, copper/silica, copper/zinc/alumina, copper/zinc oxide, palladium, Raney copper or combinations thereof. In another embodiment, the hydrogenation catalyst is a reduced metal catalyst such as reduced nickel or reduced cobalt.

The hydrogenation catalyst may be supported or unsupported. Examples of suitable support material include carbon, silica, chromia, alumina, zirconia, titania, $SiO_2$, porcelain, magnesium oxide, tin dioxide, silicon carbide, $TiO_2$, $ZrO_2$, $Al_2O_3$, aluminum silicate, steatite, zirconium silicate, cerium silicate or mixtures thereof. The hydrogenation catalyst may be used in any form, such as a uniform-composition catalyst, impregnated catalyst, coated catalyst or precipitated catalyst. Moreover, the hydrogenation catalyst may be present in the form of a shaped body, such as a sphere, ring, cylinder, cube, cuboid, tablet, lozenge, wagon wheel, star, or other geometrical body. The form of the supported catalyst may be determined by the shape of the support. Alternatively, the support may be subjected to shaping process prior to or after application of the catalytically active compound(s). Unsupported hydrogenation catalysts may be shaped by customary processes, such as by extruding or tableting.

Hydrogenation of the glycerol stream may be carried out in the gas phase, but is preferably carried out in the liquid phase with the hydrogenation catalyst being arranged in a fixed bed or as a suspension. Preferably, the hydrogenation catalyst is arranged as a fixed catalyst bed.

The first hydrogenation reactor may be any reaction vessel known to those skilled in the art such as a batch reactor, a stirred tank reactor, a semi-batch reactor, a plug flow reactor, a continuous reactor, a continuous stirred tank reactor, a slurry reactor, a fixed bed reactor, or a trickle bed reactor. Preferably, the first hydrogenation reactor is a fixed bed reactor and is configured to operate either co-currently down flow, co-currently upflow, or counter-currently. The fixed bed reactor may include a single fixed catalyst bed or plural fixed catalyst beds provided in series as a multistage. In the latter case, cooling means may optionally be provided between the fixed catalyst beds.

In certain embodiments, hydrogenation of the glycerol stream may occur within a range of about 100° C. to about 300° C., and in another embodiment within a range of about 150° C. to about 250° C., and yet in another embodiment within a range of about 200° C. to about 240° C. According to other embodiments, the hydrogenation of the glycerol stream may occur at a pressure within a range of about 100 bar to about 170 bar, and in another embodiment within a range of about 115 bar to about 150 bar, and yet in another embodiment within a range of about 130 bar to about 140 bar. The time needed to carry out the reaction may range from about 0.1 hours to about 24 hours as measured by the residence time in the first hydrogenation reactor.

According to other certain embodiments, the hydrogenation of the glycerol stream may occur under conditions where the molar ratio of hydrogen in the cycle gas to glycerol in the glycerol stream is within a range of about 600:1 to about 1:1, and in another embodiment is within a range of about 400:1 to about 1:1, and yet in another embodiment is within a range of about 10:1 to about 1:1, and in still another embodiment is within a range of about 8:1 to about 1:1. Preferably, the molar ratio of hydrogen in the cycle gas to glycerol in the glycerol stream is within a range of about 7:1 to about 1:1, and more preferably within a range of about 6:1 to about 1:1. The space velocity over the hydrogenation catalyst may generally be within a range of about 0.1 to 2 kg, preferably about 0.25 to 1 kg, and particularly preferably about 0.4 to 0.6 kg, of the glycerol stream per kg of hydrogenation catalyst per hour.

In another embodiment, the hydrogenation zone may contain a plurality of hydrogenation reactors connected in series or parallel. Preferably the hydrogenation zone contains a plurality of hydrogenation reactors connected in series. Thus, according to one embodiment, the glycerol stream and cycle gas are provided to a first hydrogenation reactor where the glycerol stream undergoes hydrogenation in the presence of a hydrogenation catalyst to form a hydrogenation reactor effluent comprising propylene glycol and glycerol, the hydrogenation reactor effluent is then optionally heated or cooled by a heat exchanger and provided to a second hydrogenation reactor (5) where the effluent undergoes further hydrogenation in the presence of a hydrogenation catalyst to produce the hydrogenated product.

Cycle gas comprising hydrogen may also be mixed with the hydrogenation reactor effluent prior to entering the second hydrogenation reactor or it may be introduced into the second hydrogenation reactor separately. Preferably, excess hydrogen is provided to the first hydrogenation reactor so that the addition of cycle gas with the hydrogenation reactor effluent or in the second hydrogenation reactor is not needed.

The second hydrogenation reactor may be any reaction vessel known to those skilled in the art such as those described above and is preferably a fixed bed reactor. The hydrogenation catalyst in the second hydrogenation reactor may be any hydrogenation catalyst such as those described above and may be the same as or different from the hydrogenation catalyst in the first hydrogenation reactor.

The temperature at which hydrogenation occurs in the second hydrogenation reactor may be within a range of about 100° C. to about 300° C., preferably within a range of about 120° C. to about 150° C.

The pressure at which hydrogenation occurs in the second hydrogenation reactor zone may be within a range of about 100 bar to about 170 bar, preferably within a range of about 115 bar to about 160 bar.

Reaction times within the second hydrogenation reactor may range from about 0.1 hours to about 24 hours, preferably from about 0.5 hours to about 6 hours, as measured by the residence time in the second hydrogenation reactor.

The space velocity over the hydrogenation catalyst in the second hydrogenation reactor may generally be within a range of 0.1 to 2 kg, preferably from 0.25 to 1 kg, and particularly preferably from 0.4 to 0.6 kg, of glycerol stream per kg of hydrogenation catalyst per hour.

Hydrogen-containing cycle gas remaining, if any, after hydrogenation, may optionally be separated from the hydrogenated product, compressed and recycled back into the hydrogenation zone for reuse. In addition, any unreacted glycerol and water remaining after hydrogenation may optionally be separated from the hydrogenated product and recycled back into the hydrogenation zone for use as part of the glycerol stream.

Where the hydrogenation catalyst is deployed in the form of a fixed bed, the hydrogenated product withdrawn as a stream from the hydrogenation zone will be essentially catalyst free with the hydrogenation catalyst being retained within the hydrogenation zone. In certain embodiments of the instant process where the hydrogenated product is produced on a continuous basis, it may be desirable to periodically or constantly regenerate all or a portion of the used hydrogenation catalyst in order to maintain optimum activity and selectivity. Suitable regeneration techniques are well-known and include, for example, calcination and solvent treatment.

Hydrogenation conversion, based on glycerol in the glycerol stream, is preferably at least 90%, and more preferably at least 95%. The selectivity, based on propylene glycol, is preferably at least 90%, more preferably, at least 95%, and even more preferably at least 97%.

According to certain embodiments, the processes described herein further include distilling the hydrogenated product produced in the first step in a distillation apparatus (6) to produce a glycol product.

Distillation of the hydrogenated product may be carried out batch-wise or continuously by conventional distillation methods. Suitable apparatuses for distillation include distillation and fractionation columns, such as tray columns which may be equipped with caps, sieve plates, sieve trays, stacked packings, dumped packings valves, side take-offs, evaporators, such as thin-film evaporators, falling film evaporators, flashing feed distributors, forced-circulation evaporators and combinations thereof. One or more distillation apparatus' may be used during the distillation step and may be connected in series or in parallel.

The distillation conditions are generally selected such that substantially all of the water and low-boiling odor compounds such as alcohols as well as a fraction of acetol in the hydrogenation product is taken overhead from the distillation apparatus by a line (7). In one embodiment, the hydrogenated product is charged to the distillation apparatus and fractionated therein under distillation conditions including a reflux ratio (L/D) of 0.9-1.5, a reflux temperature of about 180°-190° C., and a pressure within a range of about 100 mm Hg to about 760 mm Hg. In another embodiment, the column may be operated at 600 mm Hg to increase throughput through the column. However, if any color is observed in the bottoms, the pressure may be decreased and the column operated at a pressure of 100 mm Hg to about 500 mm Hg. Feed temperature to the column may be from about 220°-240° F. with a bottoms temperature ranging from about 370°-385° F. In another embodiment, the distillation apparatus may comprise a flashing feed distributor to absorb and dissipate the momentum of the liquid product, and direct the liquid product to the distributor tray floor while separating the vapor to overhead. The heavier glycol product (8) discharged from the distillation apparatus will include propylene glycol, ethylene glycol at an amount of 500 ppm to less than 2000 ppm, colorants, and odor causing compounds such as acetol, organic acids and esters having a molecular weight of greater than 132.

Figure 2:
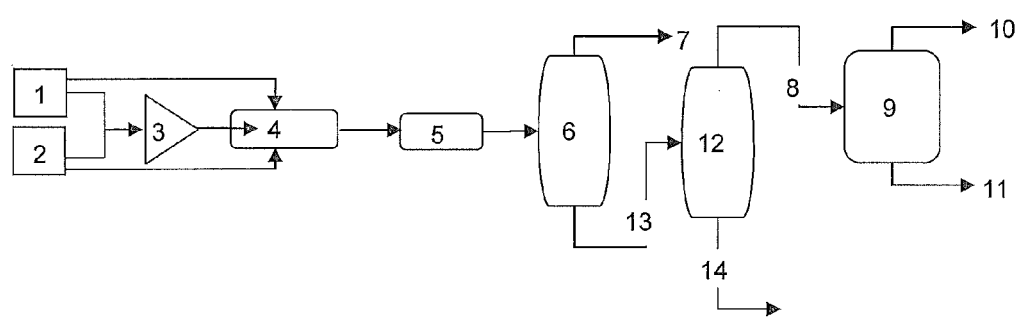
Figure 3:
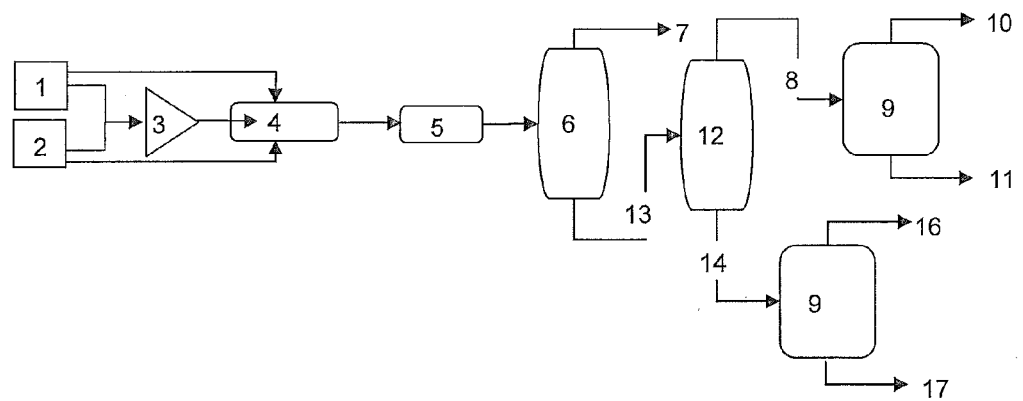

According to another embodiment, two or more distillation apparatus' may be connected in series. Referring to FIGS. 2 and 3, the hydrogenated product is charged to a first distillation apparatus (6) and fractionated therein under distillation conditions including a reflux ratio (L/D) of about 0.9-1.5, a reflux temperature of about 180°-190° C., and a pressure within a range of about 100 mm Hg to about 760 mm Hg. In another embodiment, the column may be operated at a pressure of about 600 mm Hg to increase throughput through the column. However, if any color is observed in the bottoms, the pressure may be decreased and the column operated at a pressure of about 100 mm Hg to about 500 mm Hg. Feed temperature to the column may range from abut 220°-240° F. with a bottoms temperature of about 370°-385° F. Again, the distillation conditions are selected such that substantially all of the water and low-boiling components such as alcohols as well as a fraction of acetol in the hydrogenation product is taken overhead from the first distillation apparatus as a distillate by a line (7). The heavy fraction (13) discharged from the first distillation apparatus may then be charged to a second distillation apparatus (12) and the glycol product distilled overhead under distillation conditions including a reflux ratio (L/D) of about 2.5-4.5, a reflux temperature of about 250°-260° F., and a pressure of about 30 mm Hg to about 250 mm Hg. In another embodiment, the column may be operated at a pressure of about 100 mm Hg. Feed temperature to the second distillation apparatus may range from about 280°-290° F.

with a bottoms temperature of about 330°-350° F. Again, the second distillation conditions are selected such that substantially all of the colorants have been removed from the glycol product (8), i.e. the overhead glycol product is water-white whereas a heavy by-product (14) is colored. The glycol product may include propylene glycol, ethylene glycol at an amount of less than 2000 ppm, and odor causing compounds. The heavy by-product may contain propylene glycol, ethylene glycol at an amount greater than 1% by weight based on the total weight of the heavy by-product, colorants and odor causing compounds.

According to the processes described herein a third step includes contacting the glycol product produced in the second step with a treatment bed (9) to produce industrial grade propylene glycol (10) and a waste stream (11).

In one embodiment, the treatment bed is a solid adsorbent. The solid adsorbent may be chosen, for example, from aluminas, silicas, iron oxide compounds, zeolites and carbon. The solid adsorbent may also be an ion exchange resin. Such solid adsorbents are commercially available. The adsorbent may be optionally activated prior to its use in the treatment bed, for example, an activated carbon. In one embodiment the solid adsorbent is activated by a heat treatment or a treatment intended to increase the Lewis acidity of the solid adsorbent, for example, by washing with hydrochloric acid or with nitric acid. The solid adsorbent may include combinations of the above materials.

The contacting may be performed in a fluidized bed, but it is generally preferred to place in the form of a fixed bed, through which is passed a flow of the glycol product. The fixed bed may be contained in a column or vessel and the glycol product may be passed either through the top or bottom of the column or vessel.

According to one embodiment, the fixed bed comprises carbon. Preferably, the carbon is activated carbon. The activated carbon may be activated carbon that is commercially available such as Norit A or Norit B (available from Norit Americas Inc. of Marshall, Tex.) and FILTRASORB™ 300 or 400 granular activated carbons (available from Calgon Carbon Corporation of Pittsburgh, Pa.).

The glycol product may be passed through the fixed bed comprising activated carbon at a temperature ranging from about 20°-90° C., atmospheric pressure, and a flow rate less than 1.0 m$^3$/hour. Once the activated carbon has become spent, it may be replaced or regenerated by known means, for example, by thermal treatment.

In another embodiment, the fixed bed comprises zeolite. The zeolite may be a Molecular Sieve of Type 3A, 4A, 5A or 13X. Especially preferred is Molecular Sieve of Type 13X, in the form of beads of clay/zeolite blends of a diameter of 1/16 inch to 1/8 inch.

The glycol product may be passed through the fixed bed comprising zeolite at a temperature ranging from about 20°-90° C., atmospheric pressure, and a flow rate of about 1.5 m$^3$/hour. Once spent, the zeolite may be replaced or regenerated by known means, for example, by thermal treatment.

In another embodiment, the fixed bed comprises an ion exchange resin. The ion exchange resin may be an anionic or cationic ion exchange resin or mixture thereof (herein referred to as a "mixed bed ion exchange resin").

The resins for the cationic, anionic and mixed bed ion exchangers are generally granular and porous synthetic resins typically manufactured from polymeric material such as styrene divinylbenzene, crosslinked styrene/divinylbenzene, and crosslinked acrylic copolymers such as acrylic divinylbenzene matrix, or any other material which is capable of containing active groups (e.g. sulfonic, carboxylic, phenolic, or substituted amino groups) that give the resin the property of combining with or exchanging ions between the resin and the glycol product. Preferably, the synthetic resins of this invention are manufactured from a polymer, such as the styrene divinylbenzene copolymer, that serves as a backbone support for acidic or basic functional groups. The acidic functional groups exchange cations (positively charged ions) and may be either strong or weak in acid strength. The basic functional groups exchange anions (negatively charged ions) and may be either strong or weak in base strength.

Generally, weak acid cation exchange resins are of the carboxylic acid type (—COOH) cation exchangers. Examples of such carboxylic acid type cation exchangers include carboxylic divinyl benzene copolymers, copolymers of maleic anhydride with styrene and divinyl benzene. Weak acid cation exchange resins exhibit a high affinity for hydrogen ions; that is, the resins hold on more tightly to their hydrogen ion, especially when compared to strong acid cation exchange resins.

Generally, strong acid cation exchange resins include hydrogen and sodium sulfonate resins. The strong acid cation exchanger is more willing to donate a hydrogen ion than the weak acid cation exchange resin; and thus, is more effective at removing cations from the glycol product than a weak acid cation exchange resin. As a hydrogen ion is readily released into the glycol product liquid, a counter ion (a cation) is removed and retained from the glycol product liquid by the functional group (e.g. sulfonate group) of the strong acid cation exchange resin to maintain electrical neutrality.

Generally, weak base anion exchange resins are of the aminated basic type (—NHR$_2^+$) anion exchangers. Weak base anion exchange resins exhibit a high affinity for hydroxide ions; that is, the resins hold on more tightly to their hydroxide ion, especially vis-a-vis to a strong basic anion exchange resins. Typical strong basic anion exchange resins include styrene divinylbenzene.

Examples of commercially available ion exchange resins suitable for use include DOWEX™ MWBA, DR 2030, M31 and MB50 ion exchange resins (available from The Dow Chemical Company of Midland, Mich.) and AMBERLYST™ 16 industrial grade strongly acidic catalyst (available from Rohm and Haas, a subsidiary of The Dow Chemical Company).

The glycol product may be contacted with such ion exchange resins at a temperature ranging from about 20°-90° C., atmospheric pressure, and a flow rate of about 0.75 m$^3$/hour.

Once all the available sites on the ion exchange resin have exchanged ions, the resin is exhausted and may be replaced or regenerated by known means, for example, by pumping acid through the cation beds and caustic through the anion beds or vice versa.

Referring to FIG. 3, according to the processes described herein an optional fourth step includes contacting the heavy by-product produced in the second step with a treatment bed (9) to remove colorants and produce a glycol by-product (16) and a waste stream (17) wherein the glycol by-product is colorless. The glycol by-product may include propylene glycol and ethylene glycol at an amount of greater than 1% by weight based on the total weight of the colorless glycol by-product.

The industrial grade propylene glycol may be used in various industrial and consumer applications and products. In particular, the industrial grade propylene glycol product may be used in industrial and consumer applications and products in which an odorless and colorless propylene glycol is desired. According to embodiments described herein, the industrial grade propylene glycol product may be used in heat transfer compositions, deicing compositions, food, paints, inks, and personal care compositions such as cosmetics, shampoos, shower gels, liquid hand cleansers, liquid dental compositions, skin lotions and creams, hair colorants, facial cleansers, and impregnated fluids absorbed on wiping articles.

The colorless glycol by-product may be also used in various industrial and consumer applications and products. According to embodiments described herein, the colorless glycol by-product may be used in applications and products in which odor or the amount of ethylene glycol present are not significant but the lack of color is, such as in polymer compositions or coolants, antifreeze or deicing compositions.

EXAMPLES

Example 1

Glycerol obtained during the manufacturing of biodiesel was hydrogenated in a first hydrogenation reactor in the presence of hydrogen gas and copper/chromite catalyst. The effluent from the reactor was then distilled in a distillation column packed with a high efficiency packing and the heavy fraction collected. A sample of the heavy fraction was injected into a GC-MS instrument and analyzed and the results are presented below in Table 1.

TABLE 1

|  | Retention Time | Area (%) |
|---|---|---|
| Acetaldehyde | 1.51 | 0.19 |
| Cyclic oxygenate | 1.62 | 0.11 |
| Acetone | 1.89 | 0.03 |
| Butenone | 3.07 | 0.11 |
| Oxygenate | 3.65 | 0.12 |
| Siloxane | 7.74 | 0.19 |
| Acetol | 9.23 | 4.27 |
| Siloxane | 9.96 | 0.11 |
| Substituted tetrahydrofuran | 10.46 | 0.05 |
| Phenol | 10.7 | 0.04 |
| Substituted piperidine | 11.05 | 0.18 |
| Oxygenate | 11.7 | 0.92 |
| Oxygenate | 11.74 | 0.23 |
| Substituted dioxolane | 11.78 | 0.26 |
| Cyclic oxygenate | 12.03 | 1.33 |
| Cyclic oxygenate | 12.2 | 1.08 |
| Oxygenate | 12.33 | 1.85 |
| Oxygenate | 12.41 | 0.29 |
| Propylene glycol | 12.77 | 86.2 |
| Oxygenate | 12.87 | 1.12 |
| Oxygenate | 13.06 | 0.5 |

Example 2

Glycerol obtained during the manufacturing of biodiesel was hydrogenated in a first hydrogenation reactor in the presence of hydrogen gas and a copper/chromite catalyst. The effluent from the first hydrogenation reactor was then sent to a second hydrogenation reactor and the effluent was hydrogenated in the presence of a reduced nickel catalyst. The effluent from the second hydrogenation reactor was subsequently distilled in a distillation column packed with a high efficiency packing and the heavy fraction collected. A sample of the heavy fraction was injected into a GC-MS instrument and analyzed and the results listed below in Table 2.

TABLE 2

|  | Retention Time | Area % |
|---|---|---|
| Acetol | 2.54 | 0.27 |
| Propylene glycol | 4.13 | 87.28 |
| Siloxane | 5.15 | 0.14 |
| Oxygenate | 6.72 | 0.14 |
| Ester or hydroxyl-ketone (molecular weight 132) | 6.90-7.24 | 1.08 |
| Substituted dioxolane | 7.38 | 0.81 |
| Substituted dioxolane | 7.42 | 0.89 |
| Siloxane | 7.59 | 0.83 |
| Ester or hydroxyl-ketone (molecular weight 132) | 7.74-8.44 | 8.28 |

Samples of the heavy fraction were then treated in various treatment beds and the propylene glycol product collected. A sample from each of the propylene glycol products produced from the treatment bed was injected into a GC-MS instrument and analyzed and the results listed below in Tables 3-7.

TABLE 3

Zeolite 13X Treatment Bed

|  | Retention Time | Area % |
|---|---|---|
| Oxygenates | 0.71-5.94 | 0.81 |
| Acetol | 6.10 | 0.1 |
| Propylene glycol | 9.78 | 95.38 |
| Oxygenates | 6.23-20.17 | 3.71 |

TABLE 4

Cationic Ion Exchange Resin Treatment Bed

|  | Retention Time | Area % |
|---|---|---|
| Oxygenates | 0.71-5.94 | 0.71 |
| Acetol | 6.10 | 0.05 |
| Propylene glycol | 9.78 | 95.35 |
| Oxygenates | 6.23-20.17 | 3.85 |

TABLE 5

Weak Anionic Ion Exchange Resin Treatment Bed

|  | Retention Time | Area % |
|---|---|---|
| Oxygenates | 0.71-5.94 | 2.01 |
| Acetol | 6.10 | 0.05 |
| Propylene glycol | 9.78 | 93.48 |
| Oxygenates | 6.23-20.17 | 4.46 |

TABLE 6

Cationic Ion Exchange Resin Treatment Bed

|  | Retention Time | Area % |
|---|---|---|
| Oxygenates | 0.71-5.94 | 2.78 |
| Acetol | 6.10 | 0.21 |

TABLE 6-continued

Cationic Ion Exchange Resin Treatment Bed

| | Retention Time | Area % |
|---|---|---|
| Propylene glycol | 9.78 | 92.78 |
| Oxygenates | 6.23-20.17 | 4.46 |

TABLE 7

Activated Carbon Treatment Bed

| | Retention Time | Area % |
|---|---|---|
| Oxygenates | 0.71-5.94 | 0.76 |
| Acetol | 6.10 | 0.4 |
| Propylene glycol | 9.78 | 95.92 |
| Oxygenates | 6.23-20.17 | 3.28 |

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A process for producing an industrial grade propylene glycol comprising:
   (i) providing a hydrogenation reactor effluent comprising propylene glycol and glycerol to a reactor and hydrogenating the hydrogenation reactor effluent at a temperature within a range of about 120° C. to about 150° C. and a pressure within a range of about 100 bar to about 170 bar in the presence of a hydrogenation catalyst to form a hydrogenated product;
   (ii) distilling the hydrogenated product using a distillation apparatus to form a glycol product; and
   (iii) contacting the glycol product with a treatment bed to form the industrial grade propylene glycol wherein the industrial grade propylene glycol is odorless, colorless and contains less than 2000 ppm of ethylene glycol.

2. The process of claim 1, wherein the hydrogenation reactor effluent is hydrogenated at a pressure within a range of about 115 bar to about 160 bar.

3. A process for producing a colorless and odorless industrial grade propylene glycol product comprising:
   (i) providing a glycerol stream derived from a biodiesel manufacturing process and a cycle gas comprising hydrogen to a first hydrogenation reactor and hydrogenating the glycerol stream at a temperature within a range of about 200° C. to about 240° C. and a pressure within a range of about 130 bar to about 140 bar in the presence of a first hydrogenation catalyst to form a hydrogenation reactor effluent;
   (ii) providing the hydrogenation reactor effluent to a second hydrogenation reactor and hydrogenating the hydrogenation reactor effluent at a temperature within a range of about 120° C. to about 150° C. and a pressure within a range of about 115 bar to about 160 bar in the presence of a second hydrogenation catalyst to form a hydrogenated product;
   (iii) distilling the hydrogenated product in a distillation apparatus at a reflux ratio of 0.9-1.5, a reflux temperature of about 180°-190° F., and a pressure within a range of about 100 mm Hg to about 760 mm Hg to form a glycol product; and
   (iv) contacting the glycol product with a treatment bed to form the industrial grade polypropylene glycol product, wherein the industrial grade polypropylene glycol product contains less than 2000 ppm of ethylene glycol.

* * * * *